(12) United States Patent
Mendoza et al.

(10) Patent No.: US 8,147,846 B2
(45) Date of Patent: *Apr. 3, 2012

(54) METHOD FOR THE TREATMENT OF AIRWAY DISEASES

(75) Inventors: Alberto Leonel Mendoza, Haslett, MI (US); Robert Louis Glass, Hutto, TX (US)

(73) Assignee: Board of Trustees of Michigan State University, Lansing, MI (US)

( * ) Notice: Subject to any disclaimer, the term of this patent is extended or adjusted under 35 U.S.C. 154(b) by 1068 days.

This patent is subject to a terminal disclaimer.

(21) Appl. No.: 11/296,243

(22) Filed: Dec. 7, 2005

(65) Prior Publication Data

US 2007/0128208 A1    Jun. 7, 2007

(51) Int. Cl.
*A61K 39/02*    (2006.01)
*A61K 39/00*    (2006.01)

(52) U.S. Cl. ............... 424/234.1; 424/274.1; 424/184.1

(58) Field of Classification Search ................ 424/234.1
See application file for complete search history.

(56) References Cited

U.S. PATENT DOCUMENTS 6,287,573 B1 *  9/2001  Mendoza ................... 424/234.1
6,833,136 B2 * 12/2004  Mendoza ................... 424/274.1

OTHER PUBLICATIONS

Mendoza et al., Vaccine vol. 21, pp. 2797-2804, 2003.*

* cited by examiner

*Primary Examiner* — Gary Nickol
*Assistant Examiner* — Khatol Shahnan-Shah
(74) *Attorney, Agent, or Firm* — McKee, Voorhees & Sease, P.L.C.

(57) ABSTRACT

A method for the treatment of allergic airway diseases in mammals related to Pythiosis *insidiosum* is described. The method relies upon an immunotherapeutic product of *pythium* proteins as antigens. The method is particularly useful in equine cicatrix.

10 Claims, No Drawings

METHOD FOR THE TREATMENT OF AIRWAY DISEASES

CROSS-REFERENCE TO RELATED APPLICATIONS

Not Applicable

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to a method for the treatment of an allergic airway disease in mammals caused by *Pythium insidiosum* antigens from the environment. In particular, the present invention relates to the use of an antigen immunotherapeutic product comprising at least one antigenic protein of *Pythium insidiosum* to treat the airway disease. Equines are particularly treated.

(2) Description of the Related Art

U.S. Pat. Nos. 5,948,413, 6,287,573, 6,689,571, 6,833,136 to Mendoza describe antigen vaccines of *Pythium insidiosum*. In this series of patents, the vaccines are disclosed to be used for the treatment of *Pythium insidiosum* infection (pythiosis). There are no known vaccines for the treatment of non-infecting allergic reactions to *P. insidiosum* antigens since this fungus has not been linked to such allergic reactions. U.S. Patent Application 2003/0039667 A1 to Jira describes fungal antigen oral vaccines in general.

Equine cicatrix is an allergic disease of unknown origins. This disease affects the breathing of horses. Pertinent references are:

Crawford, A. R., et al., *Mycological Res* 100 437-443 (1996);
White, T. J., et al., Amplification and direct sequencing of fungal ribosomal RNA genes for phylogenetics. In: Innis M, et al eds. *PCR protocols*. San Diego: Academic Press, 315-322 (1990);
Mendoza, L., et al., *J. Clin Microbiol* 31 2967-2973 (Abstract) (1993); (Published erratum appears in *J Clin Microbiol* 32 276 (1994);
Higgins, D. G., et al., *Comput Appl Biosci* 8 189-191 (1992) (Abstract);
Imwidthaya, P., et al., *Mycopathologia* 106 109-112 (1989) (Medline);
Thianprasit, M., et al., *Curr Top Med Mycol* 7 43-54 (1996) (Medline);
Triscott, J. A., et al., *J Cutan Pathol* 20 267-271 (1993) (Medline);
Shenep, J. L., et al., *Clin Infect Dis* 27 1388-1393 (1998) (Medline);
Virgile, R., et al., *Cornea* 12 81-83 (1993) (Medline);
Murdoch, D., et al., *Aust NZ J Ophthalmol* 25 177-179 (1997) (Medline).

OBJECTS

It is therefore an object of the present invention to provide a method for the treatment of allergic airway diseases in mammals caused by *P. insidiosum*, particularly in equines. It is further an object of the present invention to provide an immunotherapeutic product for such treatment. These and other objects will become increasingly apparent by reference to the following description.

SUMMARY OF THE INVENTION

The present invention also relates to a method for the treatment of an allergic disease caused by antigens from *Pythium insidiosum* in a mammal which comprises injecting the mammal with an effective amount of an immunotherapeutic product comprising at least one isolated protein of *Pythium insidiosum* which treats the disease. The mammals are non-human, a canine, or an equine. The mammal can also be human.

The present invention also relates to a method for the treatment of an allergic airway disease caused by antigens from *Pythium insidiosum* in a mammal which comprises injecting or orally dosing the mammal with an effective amount of an immunotherapeutic product comprising at least one isolated protein of *Pythium insidiosum* which treats the disease. Preferably the mammal is non-human. Preferably the mammal is a canine. Preferably the mammal is an equine. Preferably the mammal is human.

The present invention also relates to a method for treatment of equine allergic cicatrix disease which comprises injecting or orally dosing the equine with an effective amount of an immunotherapeutic product comprising at least one isolated protein of *Pythium insidiosum* which treats the allergic disease. Preferably the injecting is in multiple dosages over a period of time. Preferably the immunotherapeutic product comprises a sterile aqueous solution and admixture of: soluble intracellular proteins separated from disrupted cells of *Pythium insidiosum* grown in culture medium; and extracellular proteins comprising 28, 30 and 32 kD proteins as determined by SDS-PAGE electrophoresis in a supernatant from the culture medium for growing the cells of the *Pythium insidiosum* which has been separated from the cells, wherein the proteins in the admixture of the separated intracellular and extracellular proteins have been mixed with sterile distilled water and dialyzed to remove components less than 10,000 MW. Preferably the extracellular proteins have been provided by growing cells of the *Pythium insidiosum* in a culture medium, killing the cells, and then separating the killed cells from the culture medium containing the extracellular proteins and the intracellular proteins have been provided by disrupting the killed cells separated from the extracellular proteins in sterile distilled water and removing the disrupted cells from the intracellular proteins. Preferably the killed cells have been disrupted by sonication. Preferably the *Pythium insidiosum* is deposited as ATCC 74446. The *Pythium insidiosum* was deposited with the American Type Culture Collection under the Budapest Treaty as ATCC 74446. It is available upon request by name and number. All restrictions on distribution of ATCC 58463 are irrevocably removed on granting of a patent on this application. The address of the American Type Culture Collection is 10801 University Blvd., Manassas, Va. 20110-2209. Preferably the culture medium used for growing the cells is Sabouraud dextrose broth. Preferably the killed cells of *Pythium insidiosum* have been killed with thimersol or freezing in liquid nitrogen after the growing in the culture medium. Preferably the intracellular soluble proteins are separated from the disrupted cells by centrifugation. Preferably the soluble proteins which are admixed have been separated from the supernatant by being precipitated together using acetone and then the precipitate is dispersed in sterile distilled water. Preferably there are multiple isolated proteins. Preferably the proteins are a mixture of intracellular and extracellular proteins.

The present invention relates to a method for treatment of equine allergic cicatrix disease which comprises injecting or orally dosing the equine with an effective amount of an immunotherapeutic product comprising at least one isolated protein of *Pythium insidiosum* which treats the disease. Preferably the injecting is in multiple dosages over a period of time.

The substance and advantages of the present invention will become increasingly apparent by reference to the following drawings and the description.

DESCRIPTION OF THE PREFERRED EMBODIMENTS

Example

The vaccine claimed in U.S. Pat. No. 6,287,543 was used. The immunotherapeutic product is as a mixture of intracellular and extracellular proteins from *P. insidiosum* ATCC 74446 in an aqueous solution. The vaccine is USDA licensed and marketed as *Pythium* Immuno Therapeutic Product (PITP) by Pan American Vet Labs, Hulto, Tex. for the treatment of pythiosis in horses.

A total of 25 horses with clinical cicatrix were treated with the vaccine for at least 21 days. To date a significant benefit has been found in twenty-four (24) of the horses in a lessening of the breathing difficulties. Clearly the vaccine was effective.

It is intended that the foregoing description be only illustrative of the present invention and that the present invention be limited only by the hereinafter appended claims.

We claim:

1. A method for treatment of equine allergic airway disease, which comprises:
    injecting or orally dosing the equine with a treatment effective amount of an immunotherapeutic product comprising at least one isolated protein of *Pythium insidiosum* which treats the disease;
    said injecting or oral dosing occurring in multiple doses over a time period sufficient to lessen breathing difficulties.

2. The method of claim 1 wherein the treatment time period sufficient is at least 21 days.

3. The method of claim 1 wherein the immunotherapeutic product comprises in a sterile aqueous solution an admixture of:
    (a) intracellular proteins separated from disrupted cells of *Pythium insidiosum* grown in culture medium and from extracellular proteins; and
    (b) extracellular proteins comprising 28, 30 and 32 kD proteins as determined by SDS-PAGE electrophoresis in a supernatant from the culture medium for growing the cells of the *Pythium insidiosum* which has been separated from the cells, wherein the proteins in the admixture of the separated intracellular and extracellular proteins have been mixed with sterile distilled water and dialyzed.

4. The method of claim 3 wherein the extracellular proteins have been provided by growing cells of the *Pythium insidiosum* in a culture medium, killing the cells by chemical or biological agent, and separating the killed cells from the culture medium containing the extracellular proteins and the intracellular proteins which have been provided by disrupting the killed cells and removing the disrupted cells from the intracellular proteins.

5. The method of claim 4 wherein the killed cells have been disrupted by sonication or cryogenic grinding.

6. The method of claim 1 wherein the *Pythium insidiosum* is deposited as ATCC 74446.

7. The method of any one of claim 3 or 4 wherein the culture medium used for growing the cells is Sabouraud dextrose broth.

8. The method of claim 4 wherein the killed cells of *Pythium insidiosum* have been killed with thimersol, phenol or other chemical or biological agent after growing in the culture medium.

9. The method of claim 4 wherein the intracellular proteins are separated from the disrupted cells by centrifugation or filtration.

10. The method of claim 4 wherein the proteins which are admixed have been separated from the supernatant by being precipitated together using acetone and then the precipitate is dispersed in sterile distilled water.

* * * * *